(12) United States Patent
Zhang

(10) Patent No.: US 8,341,936 B2
(45) Date of Patent: Jan. 1, 2013

(54) ADVANCED EXHAUST-GAS SAMPLER FOR EXHAUST SENSOR

(75) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 112 days.

(21) Appl. No.: 12/958,168

(22) Filed: Dec. 1, 2010

(65) Prior Publication Data

US 2011/0179769 A1  Jul. 28, 2011

(51) Int. Cl.
*F01N 3/00* (2006.01)

(52) U.S. Cl. ............... 60/276; 60/274; 60/286; 60/301; 60/303

(58) Field of Classification Search .............. 60/276, 60/286, 295, 303, 274, 301
See application file for complete search history.

(56) References Cited

U.S. PATENT DOCUMENTS

| | | | |
|---|---|---|---|
| 3,343,417 A | 9/1967 | Peek, Jr. | |
| 4,199,424 A | 4/1980 | Teitelbaum | |
| 4,466,880 A | 8/1984 | Torii et al. | |
| 4,547,079 A | 10/1985 | Alamprese et al. | |
| 6,082,103 A | 7/2000 | Sugiura et al. | |
| 6,324,838 B1 | 12/2001 | Stempien et al. | |
| 6,342,141 B1 * | 1/2002 | Nelson .................... | 204/426 |
| 6,346,179 B1 * | 2/2002 | Makino et al. ........... | 204/428 |
| 6,427,439 B1 * | 8/2002 | Xu et al. ................... | 60/286 |
| 6,601,444 B2 | 8/2003 | Ohmori et al. | |
| 7,007,543 B2 * | 3/2006 | Sakawa et al. ........... | 73/23.32 |
| 7,413,641 B2 * | 8/2008 | Yamada et al. ........... | 204/428 |
| 7,434,448 B2 * | 10/2008 | Weyl et al. ............... | 73/31.05 |
| 7,559,229 B2 * | 7/2009 | Yamada .................. | 73/31.05 |
| 2007/0214862 A1 | 9/2007 | Kubinski et al. | |
| 2007/0240490 A1 | 10/2007 | Desrochers et al. | |
| 2008/0080592 A1 | 4/2008 | Houben et al. | |
| 2008/0236248 A1 | 10/2008 | Ikoma et al. | |
| 2009/0288405 A1 | 11/2009 | Shibasaki | |

FOREIGN PATENT DOCUMENTS

| | | |
|---|---|---|
| EP | 1 433 934 A2 | 6/2004 |
| JP | 357100345 A | 6/1982 |

* cited by examiner

*Primary Examiner* — Thomas Denion
*Assistant Examiner* — Diem Tran
(74) *Attorney, Agent, or Firm* — Julia Voutyras; Alleman Hall McCoy Russell & Tuttle LLP

(57) ABSTRACT

An exhaust-gas sampler is adapted to couple into an exhaust conduit and to sample a constituent of an engine exhaust flowing therein. The sampler comprises an envelope having upstream and downstream surfaces joined by a curved side surface. The upstream and downstream surfaces are each tangent to a plane substantially normal to a central axis of the exhaust conduit. A series of inlets are formed in the upstream surface, and an outlet is formed in the curved side surface. A sensor responsive to a level of the constituent in the exhaust is coupled in the envelope, at the peripheral region of the conduit.

17 Claims, 4 Drawing Sheets

ADVANCED EXHAUST-GAS SAMPLER FOR EXHAUST SENSOR

TECHNICAL FIELD

This application relates to the field of motor vehicle engineering, and more particularly, to sensing an engine-exhaust constituent.

BACKGROUND AND SUMMARY

An exhaust system of a motor vehicle may include one or more sensors responsive to exhaust constituents: nitrogen oxides ($NO_x$), ammonia, carbon dioxide, particulates, water vapor, and/or oxygen, for example. Coupled in an exhaust conduit of the exhaust system, the sensors may be used to diagnose the efficacy of emissions control, and in some cases, to modify emissions-control or engine-system parameters to improve performance. For example, the output of an ammonia sensor coupled downstream of a selective catalytic reduction (SCR) reactor may be used to regulate the amount of ammonia supplied to the SCR reactor.

To conserve space, limit costs, and accelerate warm-up, motor-vehicle exhaust sensors are typically compact, low-profile devices. This means that a sensor may sample only a relatively small portion of the exhaust flow in the conduit in which it is coupled. However, the various exhaust constituents flowing through the conduit may be distributed inhomogeneously. Accordingly, some form of homogenization or multiple-sampling may be desired so that the output of the sensor accurately reflects the area-averaged concentration of the sensed constituent.

One approach is to conduct a portion of the exhaust flow through an exhaust-gas sampling tube—e.g., a hollow tube extending radially into the exhaust conduit. The tube may include a series of inlets arranged normal to, and facing, the exhaust-flow direction in the conduit. The inlets may receive and sample the exhaust flow at several positions along the conduit radius. The sampled exhaust then travels up the tube, across the sensor element, and is discharged through an outlet hole, also normal to the flow direction, on the opposite, downstream side of the tube. However, this configuration still may not provide adequate sampling of inhomogeneously distributed constituents in an exhaust flow.

Therefore, one embodiment of this disclosure provides an improved method for sensing an engine-exhaust constituent. The method comprises separating a first exhaust flow from a second exhaust flow by admitting the first exhaust flow into an envelope. The method further comprises guiding the first exhaust flow across a sensor coupled in the envelope, and guiding the second exhaust flow over an exterior surface of the envelope to induce a pressure minimum. The method further comprises releasing the first exhaust flow from the envelope through an outlet arranged at the pressure minimum. Another embodiment provides an exhaust-gas sampler adapted to couple into an exhaust conduit and to sample a constituent of an engine exhaust flowing therein. The sampler comprises an envelope having upstream and downstream surfaces joined by a curved side surface. The upstream and downstream surfaces are each tangent to a plane substantially normal to a central axis of the exhaust conduit. A series of inlets are formed in the upstream surface, and an outlet is formed in the curved side surface. A sensor responsive to a level of the constituent in the exhaust may be coupled in the envelope, at the peripheral region of the conduit. This sensor, by virtue of the exhaust-gas sampler and related methods disclosed herein, generates an output less affected by inhomogeneous pockets of exhaust constituents and more representative of the overall composition of exhaust gas flowing through the exhaust conduit.

The summary above is provided to introduce a selected part of this disclosure in simplified form, not to identify key or essential features. The claimed subject matter, defined by the claims, is limited neither to the content of this summary nor to implementations that address problems or disadvantages noted herein.

DETAILED DESCRIPTION

Figure 1:
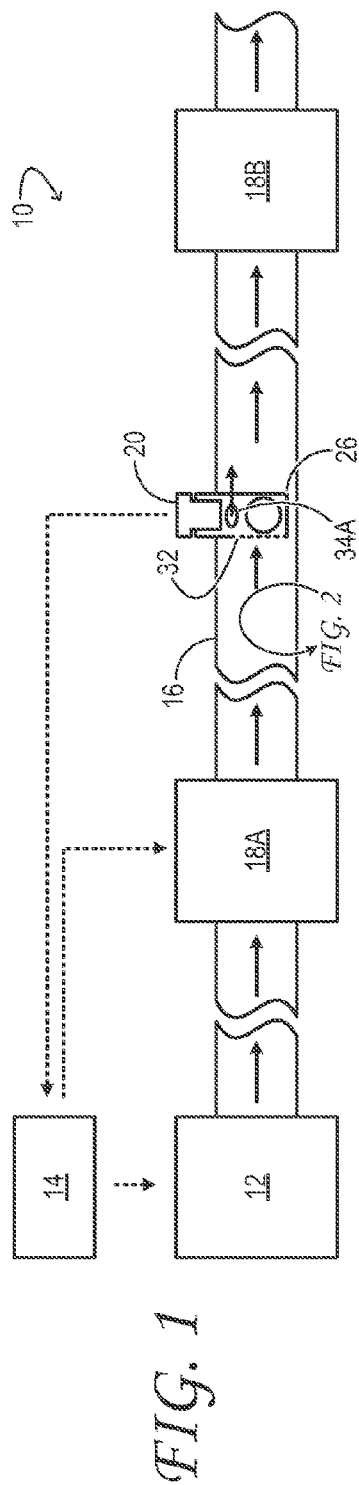
FIG. 1 shows aspects of an example engine system in accordance with an embodiment of this disclosure.

Aspects of this disclosure will now be described by example and with reference to the illustrated embodiments listed above. Components, process steps, and other elements that may be substantially the same in one or more embodiments are identified coordinately and are described with minimal repetition. It will be noted, however, that elements identified coordinately may also differ to some degree. Except as noted, the drawing figures included in this disclosure are schematic and not drawn to scale. Rather, the various drawing scales, aspect ratios, and numbers of components shown in the figures may be purposely distorted to make certain features or relationships easier to see.

FIG. 1 schematically shows aspects of an example engine system 10. The engine system includes engine 12 and controller 14. The engine admits air and fuel and generates mechanical power for driving a motor vehicle. The controller may be any electronic control system of engine system 10 or of the motor vehicle in which the engine system is installed. The controller may be configured to enact any of the various functions and operations noted herein, and other functions as well. For example, the controller may be configured to control the operation of various components of the engine—e.g., fuel injectors, throttle valves, an ignition system, exhaust-gas recirculation (EGR) valves, etc.

In combusting fuel and generating mechanical power, engine 12 discharges exhaust. The exhaust is discharged from an exhaust manifold of the engine via exhaust conduit 16. Through the exhaust conduit, the exhaust flows to various engine-system components. For example, the exhaust conduit may conduct some or all of the exhaust to an exhaust-driven turbine. The turbine may be mechanically coupled to a turbocharger compressor. The turbocharger compressor may be configured to boost the pressure of the intake air charge supplied to the engine under selected conditions. Further, the exhaust conduit may conduct some of the exhaust to an EGR system of engine system 10, via which a controlled portion of the exhaust is mixed into the intake air charge.

In the embodiment of FIG. 1, exhaust conduit 16 conducts some or all of the exhaust to exhaust-aftertreatment devices 18A and 18B. The nature, number, and arrangement of the exhaust-aftertreatment devices may differ in the different embodiments of this disclosure. In general, the exhaust-aftertreatment devices may include at least one catalyst configured to catalytically treat the exhaust flow, and thereby reduce an amount of one or more substances in the exhaust flow. For example, one catalyst may be configured to trap nitrogen oxides ($NO_x$) from the exhaust flow when the exhaust flow is lean, and to reduce the trapped $NO_x$ when the exhaust flow is rich. In other examples, a catalyst may be configured to disproportionate $NO_x$ or to selectively reduce $NO_x$ with the aid of a reducing agent. In other examples, a catalyst may be configured to oxidize residual hydrocarbons and/or carbon monoxide in the exhaust flow. Further, at least one of the exhaust-aftertreatment devices may comprise a light-off catalyst and/or a three-way catalyst. Different catalysts having any such functionality may be arranged in wash coats or elsewhere in the exhaust-aftertreatment devices, either separately or together.

The exhaust-aftertreatment devices may include a regenerable diesel-particulate filter (DPF) or soot filter. The soot filter may include a catalyst wash coat that promotes oxidation of the accumulated soot under selected conditions. The catalyst wash coat may also exhibit other emissions-control functionality, as described hereinabove. In one particular embodiment, the catalyst wash coat may include a $NO_x$ reduction catalyst, wherein 'active oxygen' evolved during $NO_x$ reduction contributes to soot oxidation.

In embodiments where an exhaust-aftertreatment device is subject to active control—e.g., active urea dosing to an SCR reactor—such control may be provided via controller 14. Accordingly, FIG. 1 shows controller 14 operatively coupled to device 18A, which may include an SCR reactor or urea injector therefor.

FIG. 1 shows exhaust sensor 20 coupled in exhaust conduit 16. The exhaust sensor provides an output—e.g., a current or voltage—responsive to a level of a constituent in the exhaust. The exhaust sensor is operatively coupled to controller 14; i.e., the controller receives the output current or voltage from the sensor.

In embodiments where device 18A is configured to reduce $NO_R$, the exhaust sensor may be a $NO_x$ sensor. The output of the sensor may be used by controller 14 to diagnose the efficacy of $NO_x$ control. It may be used in a closed-loop manner: for example, the output may be used to influence an EGR flow rate or an adjustable valve timing to keep the $NO_x$ level within acceptable limits. In another embodiment, where device 18A includes an SCR reactor configured to reduce $NO_x$ using urea or ammonia as a reductant, the exhaust sensor may be an ammonia sensor. The output of the sensor may be used by controller 14 to detect ammonia slip or to adjust reductant dosing so that ammonia slip is kept to a minimum. In another embodiment, where device 18A includes a regenerable soot filter, the exhaust sensor may be a particulate matter (PM) sensor used to diagnose the efficacy of the soot filter. In another embodiment, the exhaust sensor may be an oxygen sensor used in a closed-loop manner by controller 14 to control the supply of oxygen to the soot filter during regeneration. For this and other purposes, the controller may determine the oxygen content of the exhaust and control the same by varying fuel injection, air induction, and/or EGR. In still other embodiments, the exhaust sensor may be a carbon dioxide sensor, a water vapor sensor, etc.

Figure 2:
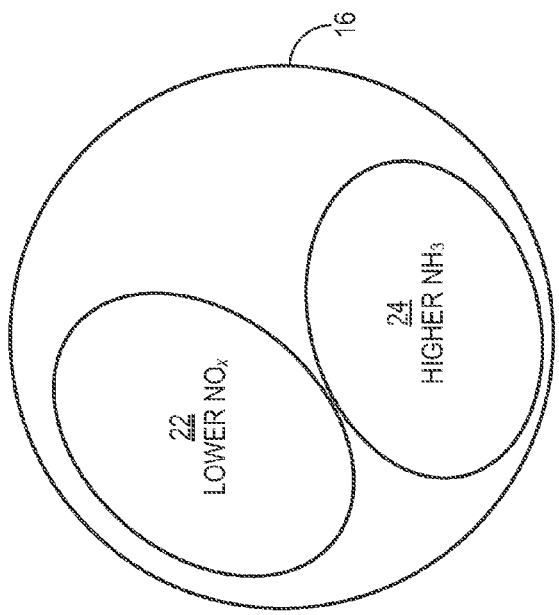
FIG. 2 shows a hypothetical, inhomogeneous distribution of exhaust constituents in a cross section of an exhaust conduit.

FIG. 2 schematically illustrates a hypothetical, inhomogeneous distribution of exhaust constituents in a cross section of exhaust conduit 16. The drawing identifies pocket 22, in which the $NO_x$ concentration is lower than the area-averaged $NO_x$ concentration in the cross section. The drawing also identifies pocket 24, in which the ammonia concentration is greater than the area-averaged ammonia concentration in the cross section. An inhomogeneous distribution of components may result from incomplete mixing of aerosolized urea solution into the exhaust flow, or from temperature gradients occurring when the solution cools a portion of the exhaust flow. Additional temperature and density gradients may result from one portion of the exhaust flowing over catalyst beds and another portion flowing around or below the catalyst beds, for example. Such gradients, evolved in an upstream exhaust-aftertreatment device, may be carried through to downstream devices, resulting in an inhomogeneous distribution propagating through the various exhaust-system components.

The inhomogeneous distribution of exhaust constituents may limit the degree to which the output of sensor 20 reflects the area-averaged concentration of the constituent it senses. This is because the sensor is typically a compact, low-profile device that responds to a local concentration. Further, the sensor may extend only short depth—ca. 1 inch, for example, in an exhaust conduit 2.5 to 6 inches in diameter.

Therefore, returning now to FIG. 1, exhaust system 10 includes exhaust-gas sampler 26, which couples exhaust sensor 20 into exhaust conduit 16. The exhaust-gas sampler is coupled into exhaust conduit 16 and configured to sample the engine exhaust flowing therein. The exhaust-gas sampler may be sealably coupled to exhaust conduit 16 in any suitable manner.

Figure 3:
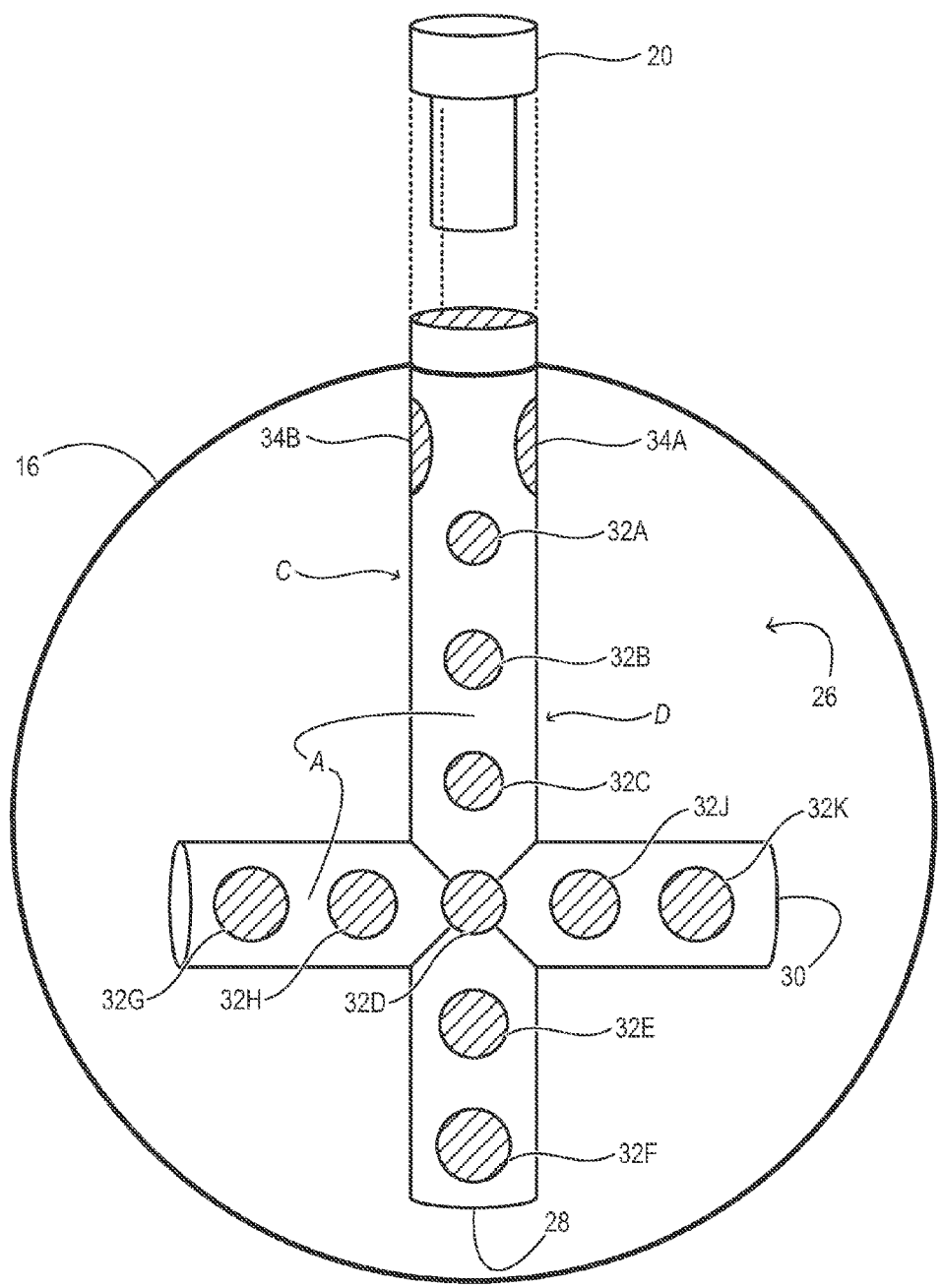
FIG. 3 is a scale drawing showing aspects of an example exhaust-gas sampler in accordance with an embodiment of this disclosure.

FIG. 3 shows aspects of one embodiment of exhaust-gas sampler 26 in greater detail. FIG. 3 is drawn to scale for the particular embodiment shown. It will be understood, however, that other embodiments fully embraced by this disclosure will admit of other dimensions, numbers of features, etc. The exhaust-gas sampler is shown from an upstream perspective inside exhaust conduit 16—i.e., looking downstream along the central axis of the exhaust conduit. In the illustrated embodiment, the exhaust-gas sampler is an envelope presenting upstream and downstream surfaces joined by a curved side surface. In FIG. 3, the upstream surface is marked A, and the side surfaces are marked C and D. The upstream and downstream surfaces are each tangent to a plane substantially normal to a central axis of conduit 16.

Exhaust-gas sampler 26 comprises a first hollow tube 28 extending radially into exhaust conduit 16 along a first direction. In the embodiment of FIG. 3, the first direction is perpendicular to the central axis of the conduit; in other embodiments, it may be oblique to the central axis. Further, while shown vertical in FIG. 3, the first tube may, in other embodiments, be rotated by any amount with respect to the central axis of the exhaust conduit.

First tube 28 has a first end exterior exhaust conduit 16 and a second end interior the exhaust conduit. The first end of the first tube is referred to as the boss end; there, exhaust sensor 20 is coupled. The opposite, interior end of the first tube may be closed. In the illustrated embodiment, the first tube has a circular cross section. In other embodiments, the cross section may be elliptical or have any other suitable shape.

In the embodiment of FIG. 3, exhaust-gas sampler 26 also comprises a second, hollow tube 30 extending within exhaust conduit 16 along a second direction different than the first direction. In the illustrated embodiment, the second tube is fully enclosed by the exhaust conduit. Like the first tube, the second tube may also have a circular or elliptical cross section. However, both ends of the second tube may be closed. The second tube intersects the first tube to define a shared interior space. In the illustrated embodiment, the first and second tubes intersect at a right angle.

In the embodiment of FIG. 3, exhaust-gas sampler 26 includes a series of inlets 32A through 34J, distributed along first tube 28 and second tube 30, on upstream surface A. Thus, the inlets are arranged normal to, and facing, the exhaust-flow direction in exhaust conduit 16. In this manner, exhaust is conducted easily into the interior space of the exhaust-gas sampler. The exhaust-gas sampler also includes outlet 34A and outlet 34B, formed in curved side surfaces C and D of the first tube. In the illustrated embodiment, the curved side surfaces guide the exhaust flow around the envelope, inducing a pressure minimum at the outlets. Accordingly, a first exhaust flow is admitted through the series of inlets and is released through the outlet. Sensor 20 is arranged in the first exhaust flow, fluidically between the inlets and the outlet.

As shown in FIG. 3, the series of inlets includes a first inlet 32A and a second inlet 32B, which is larger and arranged a greater distance from outlets 34A and 34B than the first inlet. In one embodiment, the area of each inlet may be proportional to the distance between that inlet and the outlet. In the embodiment of FIG. 3, the diameters of the various inlets may be: 3.6 millimeters (mm) for inlet 32A, 3.8 mm for inlet 32B, 4.2 mm for inlet 32C, 4.0 mm for inlet 32D, 4.55 mm for inlets 32E, 32H, and 32J, and 5.0 mm for inlets 32F, 32G, and 32K. In these embodiments, the increasing size of the inlets compensates for the increased resistance to flow caused by the longer flow path. As a result, a more equivalent mass flow of exhaust may be admitted through each of the inlets. The exhaust, therefore, may be sampled from the various regions of exhaust conduit 16 at roughly equal rates, despite unequal distance from the outlets and the sensor. In the embodiment of FIG. 3, each of the inlets admits between 6 and 16 percent of the combined mass flow through the outlets.

Figure 4:
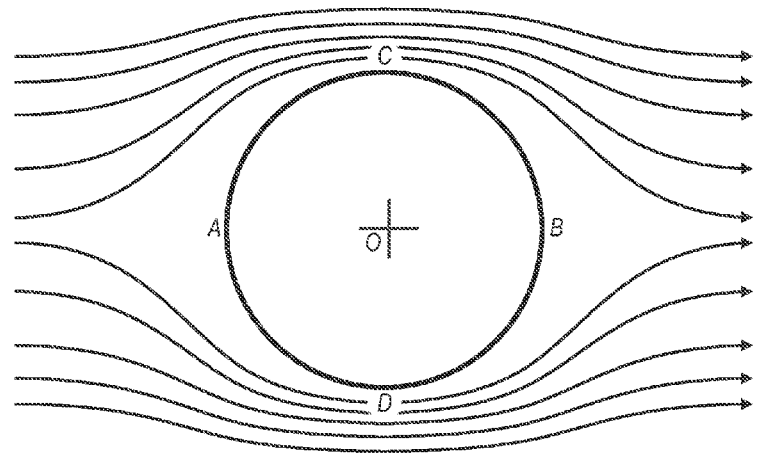
FIG. 4 shows fluid flow around a tube having a circular cross section.
Figure 5:
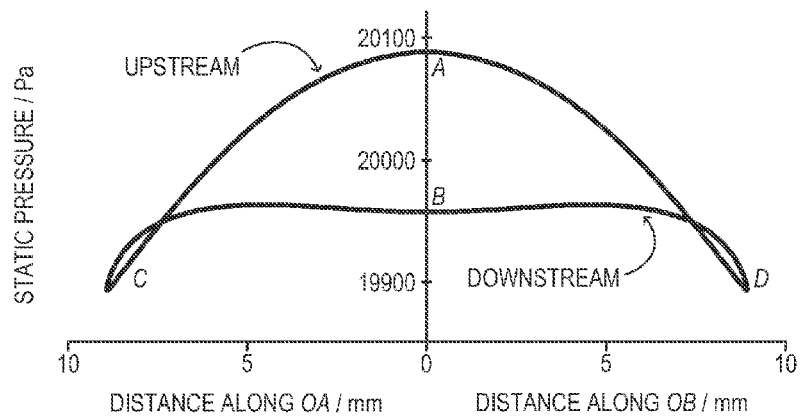
FIG. 5 graphically shows a result of a fluid-dynamics calculation in accordance with the structure illustrated in FIG. 4.

Additional advantages of the configurations here disclosed will be apparent from examining FIGS. 4 and 5. FIG. 4 shows fluid flow around a tube, such as first tube 28 or second tube 30. The location marked A in FIG. 4 corresponds to the upstream surface, the location marked B corresponds to the downstream surface, on the opposite side of the tube, and the locations marked C and D correspond to the curved side surfaces of the tube.

FIG. 5 graphically shows a result of a fluid-dynamics calculation based on the structure in FIG. 4. This result shows that gas flow around the tube, from the upstream surface to the downstream surface causes a static pressure variation along the exterior of the tube—i.e., static with respect to gas flow inside the tube. Further, the greatest differential in the static pressure is from the upstream flow region A to either of the exterior side regions C and D, not to downstream flow region B. In other words, there is a greater flow potential between points A and C than between points A and B. In some scenarios, this can result in a 15 percent increase in the exhaust flow rate through the tube, relative to an otherwise similar configuration in which the outlet is arranged at downstream surface B. Accordingly, the inlets and outlets of the exhaust-gas samplers disclosed herein are located to take advantage of this effect.

The configurations described above enable various methods for sensing an engine-exhaust constituent. Accordingly, some such methods are now described, by way of example, with continued reference to the above configurations. It will be understood, however, that the methods here described, and others fully within the scope of this disclosure, may be enabled by other configurations as well. Naturally, some of the process steps described and/or illustrated herein may, in some embodiments, be omitted without departing from the scope of this disclosure. Likewise, the indicated sequence of the process steps may not always be required to achieve the intended results, but is provided for ease of illustration and description. One or more of the illustrated actions, functions, or operations may be performed repeatedly, depending on the particular strategy being used. Moreover, the various control and estimation routines disclosed herein may include one or more different processing strategies such as event-driven, interrupt-driven, multi-tasking, multi-threading, and the like. As such, at least some of the disclosed process steps (operations, functions, and/or acts) may represent code to be programmed into computer readable storage medium in a controller.

Figure 6:
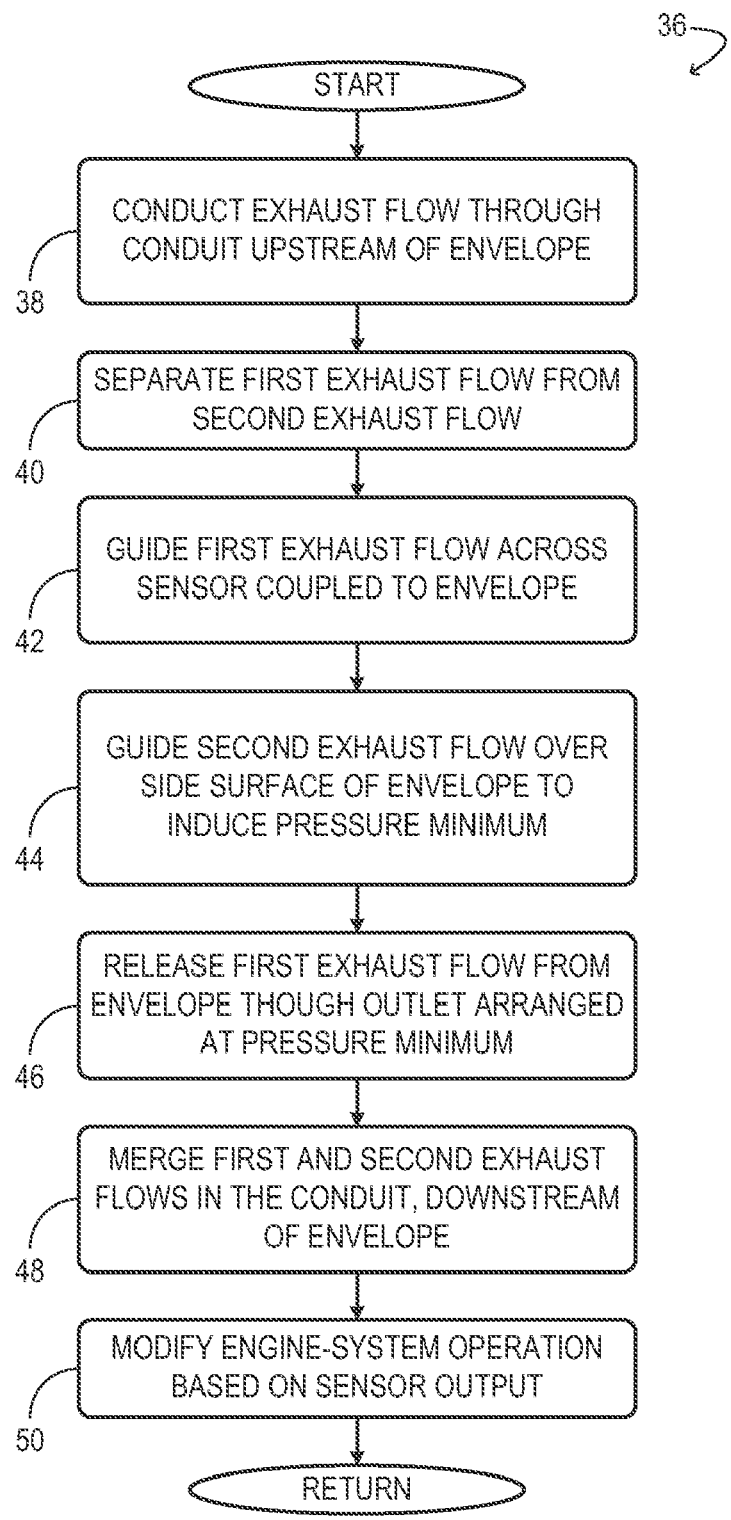
FIG. 6 illustrates an example method for sensing an engine-exhaust constituent in accordance with an embodiment of this disclosure.

FIG. 6 illustrates an example method 36 for sensing an engine-exhaust constituent in one embodiment. At 38 an exhaust flow is conducted through an exhaust conduit, upstream of an envelope. The envelope may be the surface of an exhaust-gas sampler, as described above. At 40 a first exhaust flow is separated from a second exhaust flow by admitting the first exhaust flow into the envelope. In this context, the first and second exhaust flows are merely first and second subflows separated from the combined flow upstream of the envelope. Admitting the first exhaust flow into the envelope may comprise admitting through a series of inlets formed in an upstream surface of the envelope, where a plane tangent to the upstream surface is substantially normal to a central axis of the exhaust conduit. With this configuration, the first exhaust flow is admitted into the envelope from different regions of the exhaust conduit. Further, the exhaust may be admitted with less restriction from regions of the conduit farther from the outlet, and with greater restriction from regions of the conduit closer to the outlet. Such restriction may be controlled by controlling the relative sizes of the inlets, as described hereinabove.

At 42 the first exhaust flow is guided across a sensor coupled in envelope; the sensor is configured such that an output of the sensor changes in response to an amount of the sensed constituent in the first exhaust flow. Accordingly, the exhaust in the conduit is delivered to the sensor via a sampling strategy. For example, the exhaust in the conduit may be sampled along first and second directions parallel neither to each other nor to the central axis of the conduit.

At 44 the second exhaust flow—the remaining exhaust flow after the first flow has been separated out—is guided over an exterior surface of an envelope to induce pressure minimum. In one embodiment, the pressure minimum may be induced at a curved side surface of the envelope, where a plane tangent to the side region is parallel or oblique to a central axis of the conduit.

At 46 the first exhaust flow is released from the envelope though an outlet arranged at the pressure minimum. In one embodiment, the first exhaust flow may be released from two outlets arranged opposite each other. At 48 the first and second exhaust flows are merged in the exhaust conduit, downstream of the envelope.

At 50 an engine-system operation is modified based on an output of the sensor. In one particular embodiment, the constituent sensed by the sensor may be ammonia. Accordingly, this method may be applied to controlling reductant dosing and thereby controlling ammonia slip from an engine exhaust system equipped with an SCR reactor. Accordingly, the method may further comprise controlling reductant dosing to an SCR reactor disposed upstream of the envelope in response to the output of the sensor. From 50, method 36 returns.

Finally, it will be understood that the articles, systems, and methods described hereinabove are embodiments of this disclosure—non-limiting examples for which numerous variations and extensions are contemplated as well. Accordingly, this disclosure includes all novel and non-obvious combinations and sub-combinations of the articles, systems, and methods disclosed herein, as well as any and all equivalents thereof.

The invention claimed is:

1. An exhaust-gas sampler adapted to couple into an exhaust conduit and to sample exhaust flowing therein, comprising: an envelope having upstream and downstream surfaces, each tangent to a plane normal to a central axis of the exhaust conduit, joined by a curved side surface with an outlet formed therein, and a series of inlets formed in the upstream surface, an area of each inlet proportional to a distance between that inlet and the outlet.

2. The sampler of claim 1, wherein the curved side surface guides the exhaust around the envelope, inducing a pressure minimum at the outlet.

3. The sampler of claim 1, wherein the series of inlets includes a first inlet and a second inlet larger than the first inlet, and wherein the second inlet is arranged a greater distance from the outlet than the first inlet.

4. The sampler of claim 1 further comprising a sensor coupled in the envelope, at a peripheral region of the conduit, wherein the sensor is responsive to a level of a constituent in the exhaust.

5. The sampler of claim 4, wherein a first exhaust flow is admitted through the series of inlets and released through the outlet, and wherein the sensor is arranged in the first exhaust flow fluidically between the inlets and the outlet.

6. The sampler of claim 4, wherein the envelope comprises a tube extending into the conduit along a first direction, wherein the tube has a first end exterior the conduit and a second, closed end interior the conduit, and wherein the sensor is coupled to the first end.

7. The sampler of claim 6, wherein the first direction is perpendicular or oblique to the central axis of the exhaust conduit.

8. The sampler of claim 6, wherein the tube comprises a circular or elliptical cross section.

9. The sampler of claim 6, wherein the tube is a first tube, and wherein the envelope comprises a second tube extending within the conduit along a second direction different than the first, and wherein the second tube intersects the first tube to define a shared interior space.

10. The sampler of claim 4, wherein the constituent is one or more of nitrogen oxides, ammonia, carbon dioxide, particulate matter, water vapor, and oxygen.

11. A method for sensing an engine-exhaust constituent, comprising:
separating a first exhaust flow from a second exhaust flow by admitting the first exhaust flow into an envelope;
guiding the first exhaust flow across a sensor coupled in the envelope;
guiding the second exhaust flow over an exterior surface of the envelope to induce a pressure minimum;
releasing the first exhaust flow from the envelope through an outlet arranged at the pressure minimum;
conducting the first and second exhaust flows, prior to separation, through an exhaust conduit upstream of the envelope; and
merging the first and second exhaust flows in the conduit downstream of the envelope, wherein admitting the first exhaust flow into the envelope comprises sampling exhaust in the conduit along first and second directions parallel neither to each other nor to a central axis of the conduit.

12. The method of claim 11, wherein the pressure minimum is induced at a curved side surface of the envelope, and wherein a plane tangent to the curved side surface is parallel or oblique to the central axis of the exhaust conduit.

13. The method of claim 11, wherein admitting the first exhaust flow into the envelope comprises admitting through a series of inlets formed in an upstream surface of the envelope, and wherein a plane tangent to the upstream surface is normal to the central axis of the exhaust conduit.

14. The method of claim 11, wherein admitting the first exhaust flow into the envelope comprises admitting exhaust from different regions of the exhaust conduit, such that the exhaust is admitted with less restriction from regions of the conduit farther from the outlet, and with greater restriction from regions of the conduit closer to the outlet.

15. The method of claim 11, wherein an output of the sensor changes in response to an amount of the constituent in the first exhaust flow, wherein the constituent is ammonia, the method further comprising controlling reductant dosing to a selective catalytic reduction reactor coupled upstream of the envelope, in response to the output of the sensor.

16. An exhaust-gas sampler adapted to couple into an exhaust conduit and to sample a constituent of an engine exhaust flowing therein, the sampler comprising:
a first tube extending into the conduit along a first direction, perpendicular or oblique to a central axis of the conduit, the first tube having a first end exterior the conduit, a second end interior the conduit, and upstream and downstream surfaces joined by a curved side surface;
a series of inlets formed in the upstream surface;
an outlet formed in the curved side surface;
a second tube extending into the conduit along a second direction, different than the first, the second tube intersecting the first tube to define a shared interior space; and
a sensor coupled to the first end of the first tube, the sensor responsive to a level of the constituent in the exhaust.

17. The sampler of claim 16, wherein the first and second tubes each comprise a circular or elliptical cross section.

* * * * *